(12) United States Patent
Chiu et al.

(10) Patent No.: US 8,475,397 B2
(45) Date of Patent: Jul. 2, 2013

(54) PLANTAR FASCIITIS REHABILITATION CONTROLLING DEVICE

(75) Inventors: Ching-Hua Chiu, Taichung (TW); Li-Wei Chou, Taichung (TW)

(73) Assignee: China Medical University, Taichung (TW)

( * ) Notice: Subject to any disclaimer, the term of this patent is extended or adjusted under 35 U.S.C. 154(b) by 262 days.

(21) Appl. No.: 12/974,338

(22) Filed: Dec. 21, 2010

(65) Prior Publication Data

US 2011/0172578 A1 Jul. 14, 2011

(30) Foreign Application Priority Data

Jan. 8, 2010 (TW) ................................ 99100338 A (51) Int. Cl.
*A61F 5/00* (2006.01)
(52) U.S. Cl.
USPC ........ 602/28; 602/5; 602/16; 602/17; 602/32; 128/882
(58) Field of Classification Search
USPC 602/5, 16, 23, 27–28, 32; 128/882; D24/190, D24/192
See application file for complete search history.

(56) References Cited

U.S. PATENT DOCUMENTS 6,110,078 A * 8/2000 Dyer .............................. 482/79

* cited by examiner

*Primary Examiner* — Patricia Bianco
*Assistant Examiner* — Camtu Nguyen
(74) *Attorney, Agent, or Firm* — Rosenberg, Klein & Lee (57) ABSTRACT

The present invention relates to a plantar fasciitis rehabilitation controlling device. It mainly comprises a securing portion, a rotatable portion, a torque pivoting portion, a pulling portion, and a controller. The securing portion and the rotatable portion are provided for securing a user's shank and foot. This torque pivoting portion can create a torque causing the rotatable portion moving back. The pulling portion has a controller so as to pull the rotatable portion to rotate between a first angle and a second angle so that it can reduce possibility of the plantar fasciitis and ease pain of the plantar fasciitis. Hence, this invention can achieve an active rehabilitation exercise. The belt's pulling interval time can be adjusted. It has a safety switch to ensure its product safety. It is convenient that the user can use a wireless device to operate this system. In addition, the user can be informed about current condition via an audio device.

12 Claims, 8 Drawing Sheets

PLANTAR FASCIITIS REHABILITATION CONTROLLING DEVICE

BACKGROUND OF THE INVENTION

1. Field of the Invention

The present invention relates to a plantar fasciitis rehabilitation controlling device. In which, it can achieve an active rehabilitation exercise. The belt's pulling interval time can be adjusted. Also, it has a safety switch to ensure its product safety. It is convenient that the user can use a wireless device to operate this device. In addition, the user can be informed about current condition via an audio device.

2. Description of the Prior Art

Figure 11:
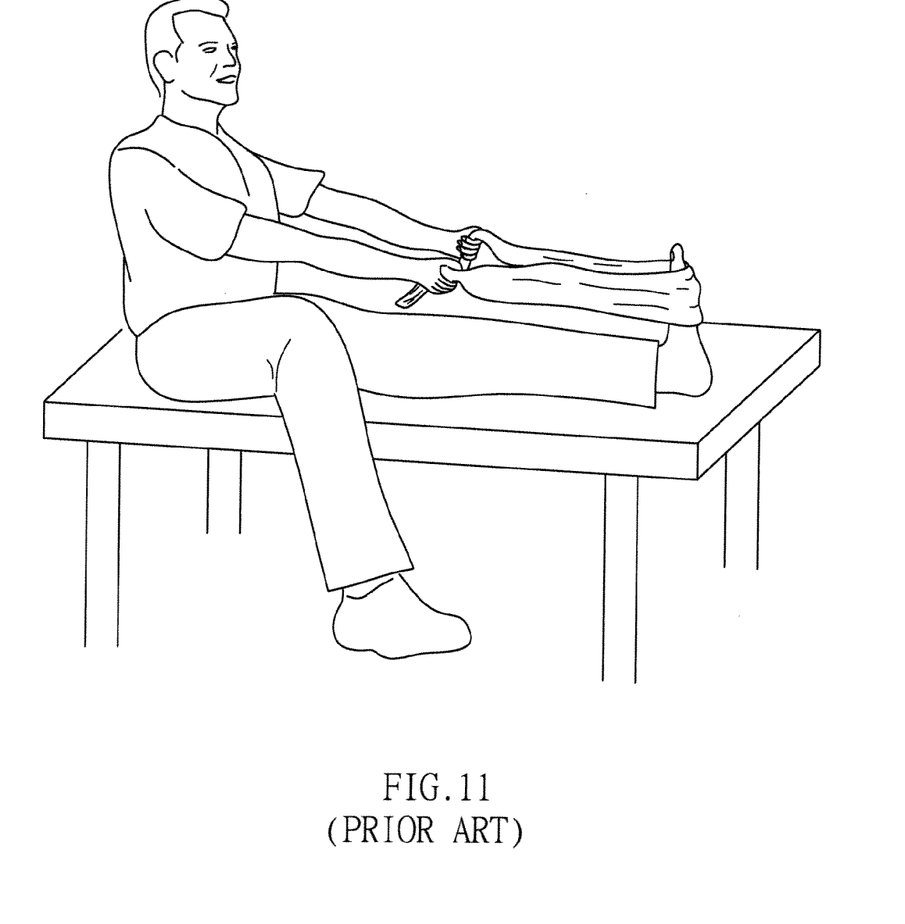
FIG. 11 is a perspective view showing the traditional manual method about the plantar fasciitis rehabilitation.

With regard to plantar fasciitis, the traditional treatment is to use a towel pulling a foot, as exhibited in FIG. 11. Such pulling action is able to enhance the pliancy of plantar fascia and tendon. By utilizing this way, the user has to use both hands for firmly grasping this towel and pulling this towel. Then, the foot will become tilted. However, the user needs to apply a lot of physical strength. If the user wants to keep applying force constantly, it is a fatigued work. Besides, it is difficult to control the magnitude of the applied force as well as to keep the applied force stable for a long time. In addition, the user cannot do such pulling action when this user is sleeping or taking a rest on a bed. About the towel, it is easy to slip away from the foot or to jam in the recessed portion of the foot which causes the applied force extremely uneven. The above-mentioned drawbacks are troublesome.

Furthermore, it is possible to design a mechanical device to replace the human's hands for creating a pulling force. Although it can save the user's physical strength, it still has the following potential problems.

[1] It cannot set a precise pulling force and a precise tilted angle of the foot.

[2] It cannot set a pulling time.

[3] It cannot generate a reciprocated movement automatically.

[4] The user cannot operate it by wireless control.

[5] There is no audio notice of the current condition for the user.

SUMMARY OF THE INVENTION

The primary object of the present invention is to provide a plantar fasciitis rehabilitation controlling device. In which, it can achieve an active rehabilitation exercise.

The second object of the present invention is to provide a plantar fasciitis rehabilitation controlling device. The belt's pulling interval time can be adjusted.

The next object of the present invention is to provide a plantar fasciitis rehabilitation controlling device. It has a safety switch to ensure its product safety.

A further object of the present invention is to provide a plantar fasciitis rehabilitation controlling device. It is convenient that the user can use a wireless device to operate this device.

Another object of the present invention is to provide a plantar fasciitis rehabilitation controlling device. The user can be informed about current condition via an audio device.

In order to achieve the above mentioned objects, this invention is provided. A plantar fasciitis rehabilitation controlling device comprising:

a securing portion for securing a user's shank;
a rotatable portion for securing a user's foot;
a torque pivoting portion connected with the securing portion and the rotatable portion so as to create a torque causing the rotatable portion moving back;
a pulling portion having a first end portion and a second end, the first end portion being pivoted on the securing portion, the second end portion connecting with the rotatable portion; and
a controller being disposed between the first end portion and the second end portion so as to pull the rotatable portion to rotate between a first angle and a second angle so that it can reduce possibility of plantar fasciitis occurrence or reduce symptoms of plantar fasciitis.

DETAILED DESCRIPTION OF THE PREFERRED EMBODIMENT

As shown in FIGS. 1, 2, 3A, 3B and 4, this invention relates to a plantar fasciitis rehabilitation controlling device. It mainly comprises a securing portion 10, a rotatable portion 20, a torque pivoting portion 30, a pulling portion 40, and a controller 43.

Concerning this securing portion 10, it is provided for securing a user's shank 91.

About this rotatable portion 20, it is provided for securing a user's foot 92.

With regard to the torque pivoting portion 30, it is connected with the securing portion 10 and the rotatable portion 20 so as to create a torque causing the rotatable portion 20 moving back.

The pulling portion 40 has a first end portion 41 and a second end portion 42 (which is a resilient belt). The first end portion 41 is pivoted on the securing portion 10. The second end portion 42 connects with the rotatable portion 20.

With reference to this controller 43, it is disposed between the first end portion 41 and the second end portion 42 so as to pull this rotatable portion 20 to rotate between a first angle θ1 and a second angle θ2 so that it can reduce possibility of plantar fasciitis occurrence or reduce symptoms of plantar fasciitis.

Figure 1:
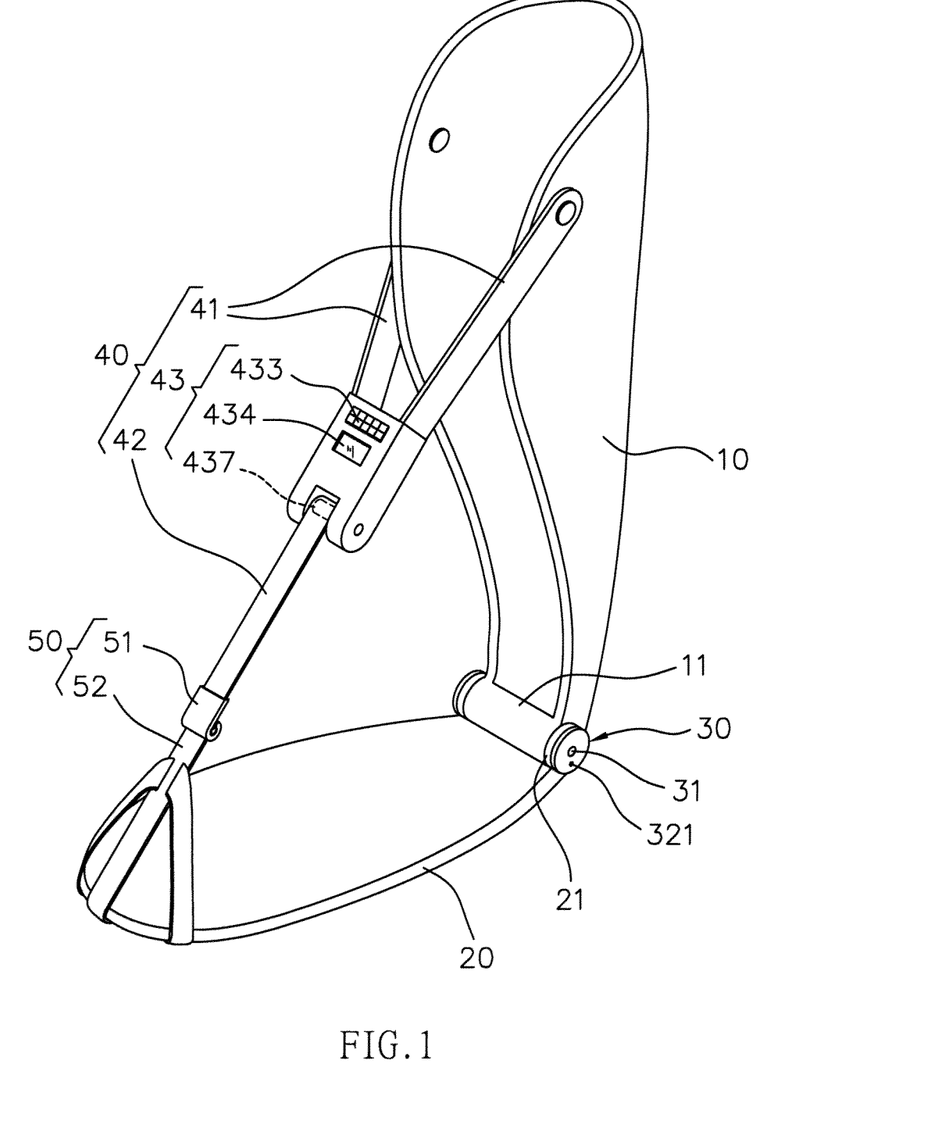
FIG. 1 is a perspective view of the present invention.
Figure 2:
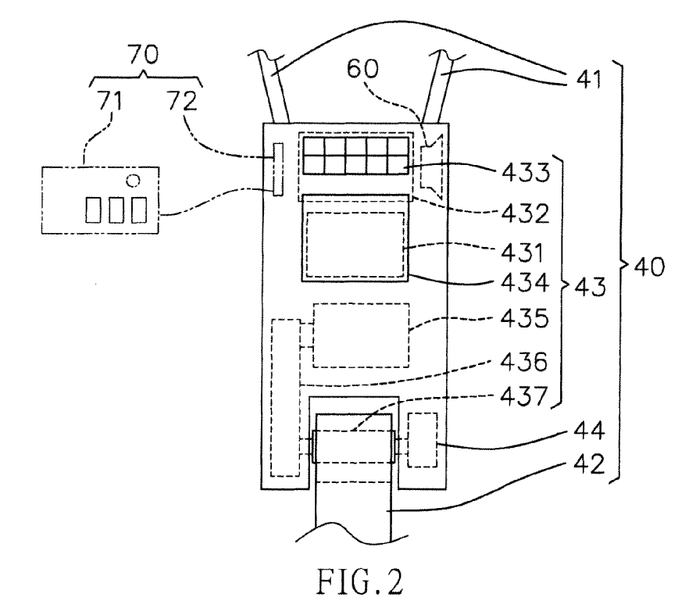
FIG. 2 is a view showing a portion of the structure of this invention.
Figure 3A:
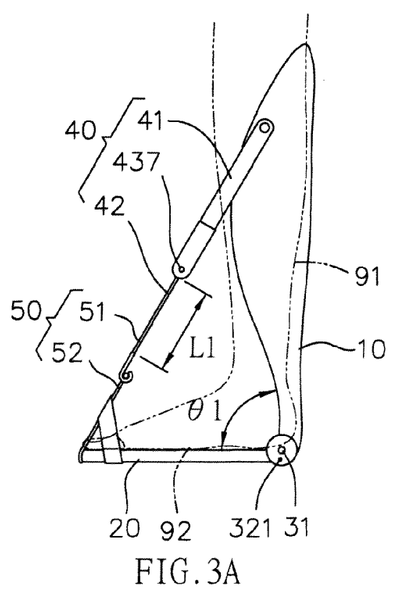
FIG. 3A and 3B show the conditions of the rotatable portion before it rotating and after it rotating toward the securing portion.
Figure 3B:
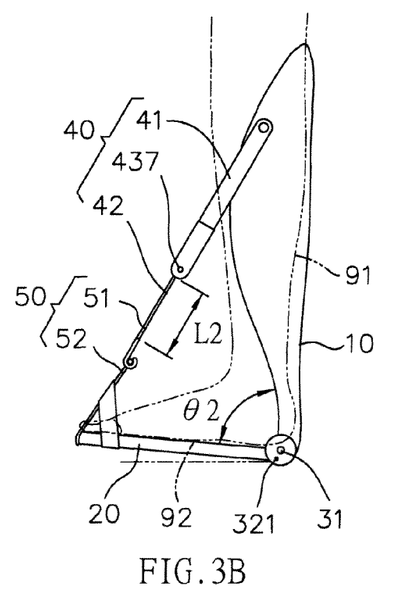
Figure 4:
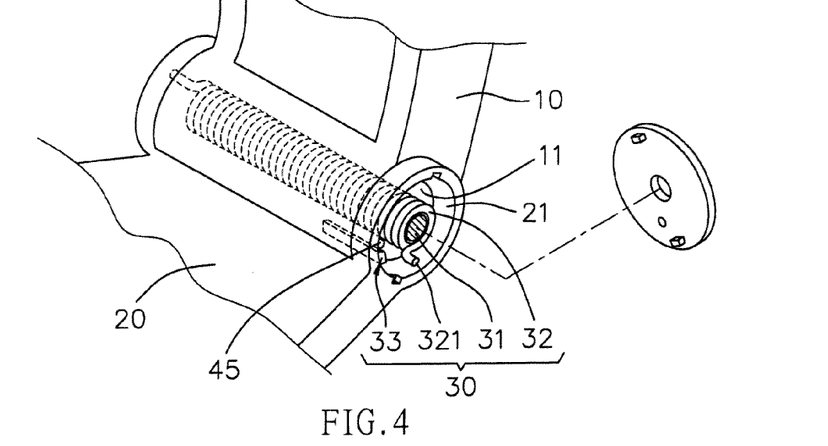
FIG. 4 is a view showing the pivoting part of this invention.

Practically, the securing portion 10 contains a pivoting part 11.

This rotatable portion 20 has a pair of pivoting receivers 21.

Moreover, the torque pivoting portion 30 includes a shaft 31, a torque element 32, and a limit controller 33.

About this shaft 31, it is disposed in the pivoting part 11 and the pivoting receivers 21. This shaft 31 is pivoted with the securing portion 10 and the rotatable portion 20.

With regard to the torque element 32, it fits on the shaft 31. For example, this torque element 32 could be a conventional torque spring for generating a force to pull the rotatable portion 20 back. In addition, the torque element 32 at least includes a touching end 321.

Figure 5A:
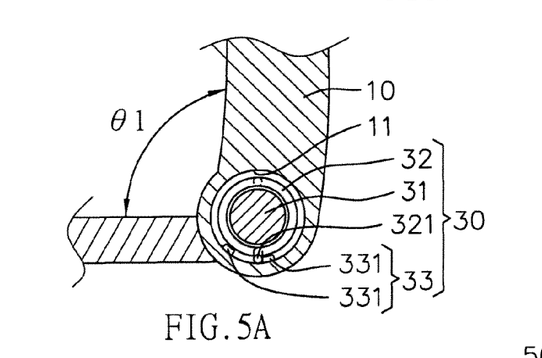
FIG. 5A and 5B shows the conditions about the torque pivoting portion before rotating and after rotating.
Figure 5B:
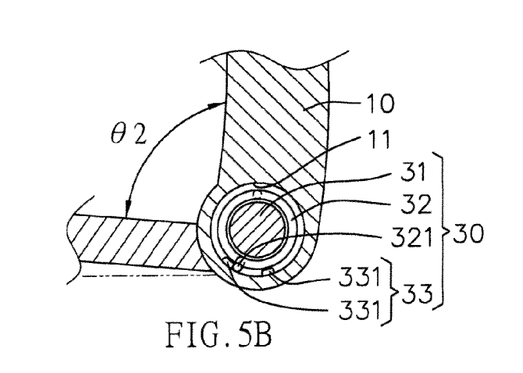

Concerning the limit controller 33, it includes one limit switch 331 corresponding to the first angle θ1 and another limit switch 331 corresponding to the second angle θ2. Both limit switches 331 (as illustrated in FIG. 5A and 5B) are disposed in the pivoting part 11. These limit switches 331 can be touched and activated by the touching end 321.

Figure 7:
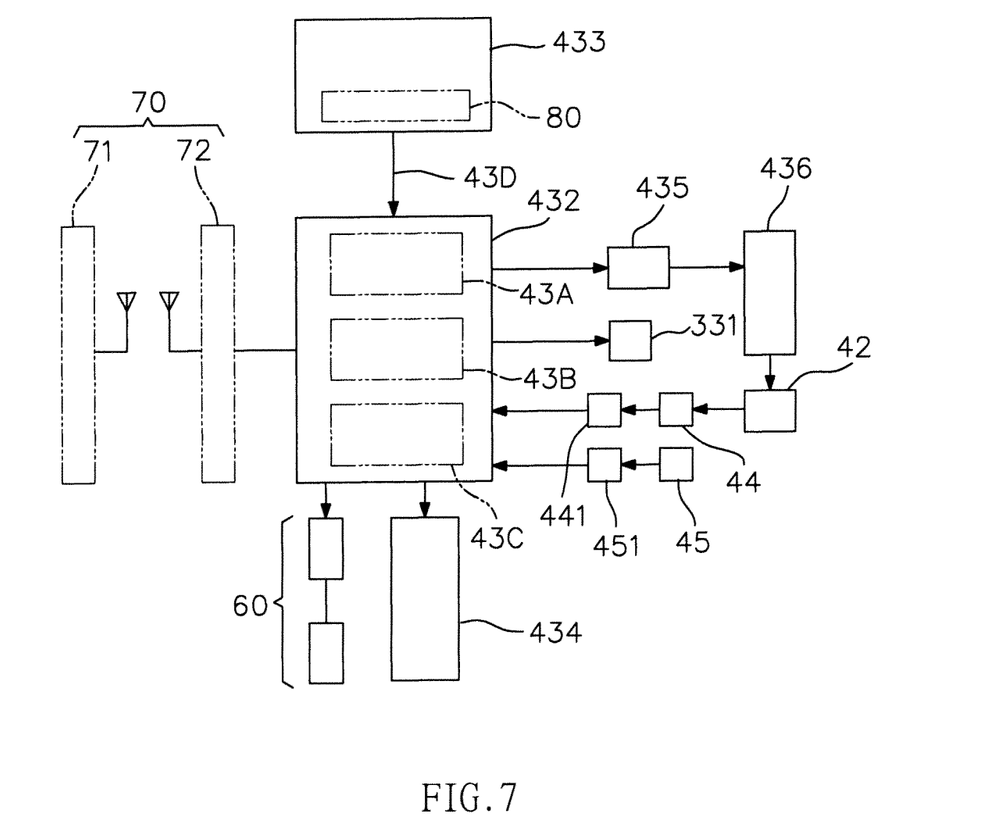
FIG. 7 illustrates the operation process of the present invention.

Furthermore, with regard to this controller 43, it includes:
a power source 431 which is a battery for providing power to the controller 43;
a controlling circuit module 432 (as illustrated in FIG. 7) having a central processing unit 43A, a random access memory 43B (or called RAM), and a read only memory 43C (or called ROM); the controlling circuit module 432 being provided for pulling/releasing the rotatable portion 20;
an input portion 433 for inputting at least one controlling information 43D to the controlling circuit module 432;
a display 434 for showing the controlling information 43D of the input portion 433;
a driving portion 435 which is an electric motor controlled by the controlling circuit module 432 according to the controlling information 43D;
a reduction device 436 (such as reduction gears) for reducing an output of the driving portion 435 into another slower output;
a rolling portion 437 which is pulley, the second end portion 42 being pulled/released by the reduction device 436 so as to rotate the rotatable portion 20.

About the pulling portion 40, it includes:
[a] a torque sensor 44 connecting with the rolling portion 437 for detecting torque and sending out a signal to the controller 43 via an analog/digital converter 441; and
[b] an angle detector 45 disposed on the pivoting portion 11 for detecting rotation angle of the rotatable portion 20 and sending out another signal to the controller 43 via another analog/digital converter 451.

Figure 6:
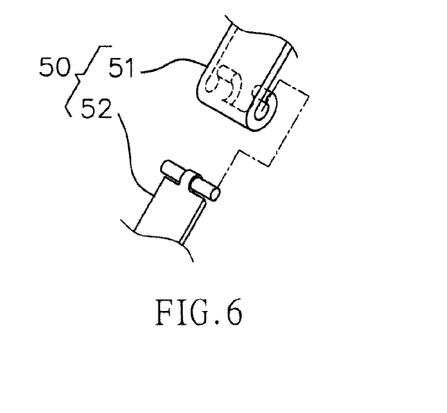
FIG. 6 is a view of the locking portion of the present invention.

It is optional that this invention further comprises:
[a] a locking portion 50 having a male locker 51 and a female locker 52 (as shown in FIG. 6), the locking portion 50 being disposed on the second end portion 42 so that the user can install/detach it conveniently;
[b] an audio device 60 for generating voice messages about current condition;
[c] a wireless device 70 including a wireless transmitter 71 and a wireless receiver 72 which is electrically connected to the controller 43; and
[d] a safety switch 80 for deactivating the pulling portion 40 in an emergency (such as the user's leg has a spasm or becomes quite uncomfortable).

Regarding this invention, it at least includes the following two operating modes.

Figure 8:
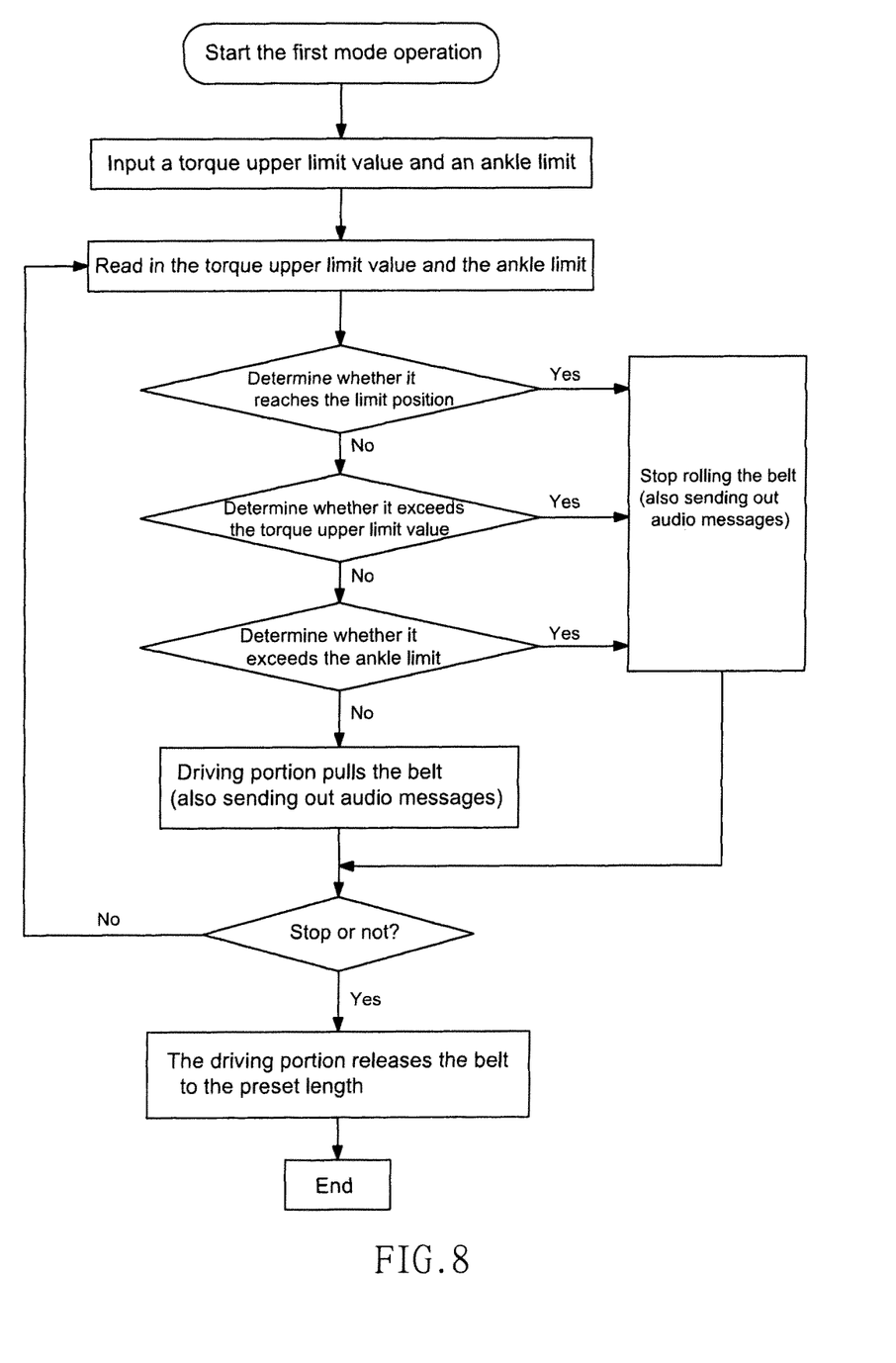
FIG. 8 shows a flowchart of the first operation mode of this invention.
Figure 10A:
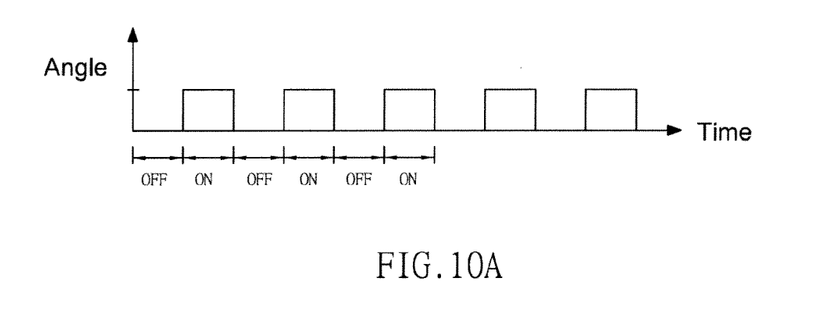
FIG. 10A shows the relationship between the rotation angle and time in the first operation mode.

[a] Fixed operating mode (or called the first operation mode). As illustrated in FIGS. 8 and 10A, the user can input a torque upper limit value and an ankle limit via the input portion 433. After which, the driving portion 435 is turned on. The driving portion 435 drives the rolling portion 437 to generate a repeated clockwise rotation and counterclockwise rotation alternately via the reduction device 436. Hence, the rolling portion 437 makes the second end portion 42 pulling and releasing repeatedly. Also, under the preset torque upper limit value and the ankle limit, the user's foot 92 only rotates between the first angle θ1 and the second angle θ2 (repeated ON, OFF, ON, OFF, etc.). Such repeated exercise is helpful to reduce the possibility of plantar fasciitis occurrence or to ease the pain caused by plantar fasciitis. Therefore, it effectuates an active intrinsic toe exercise.

Figure 9:
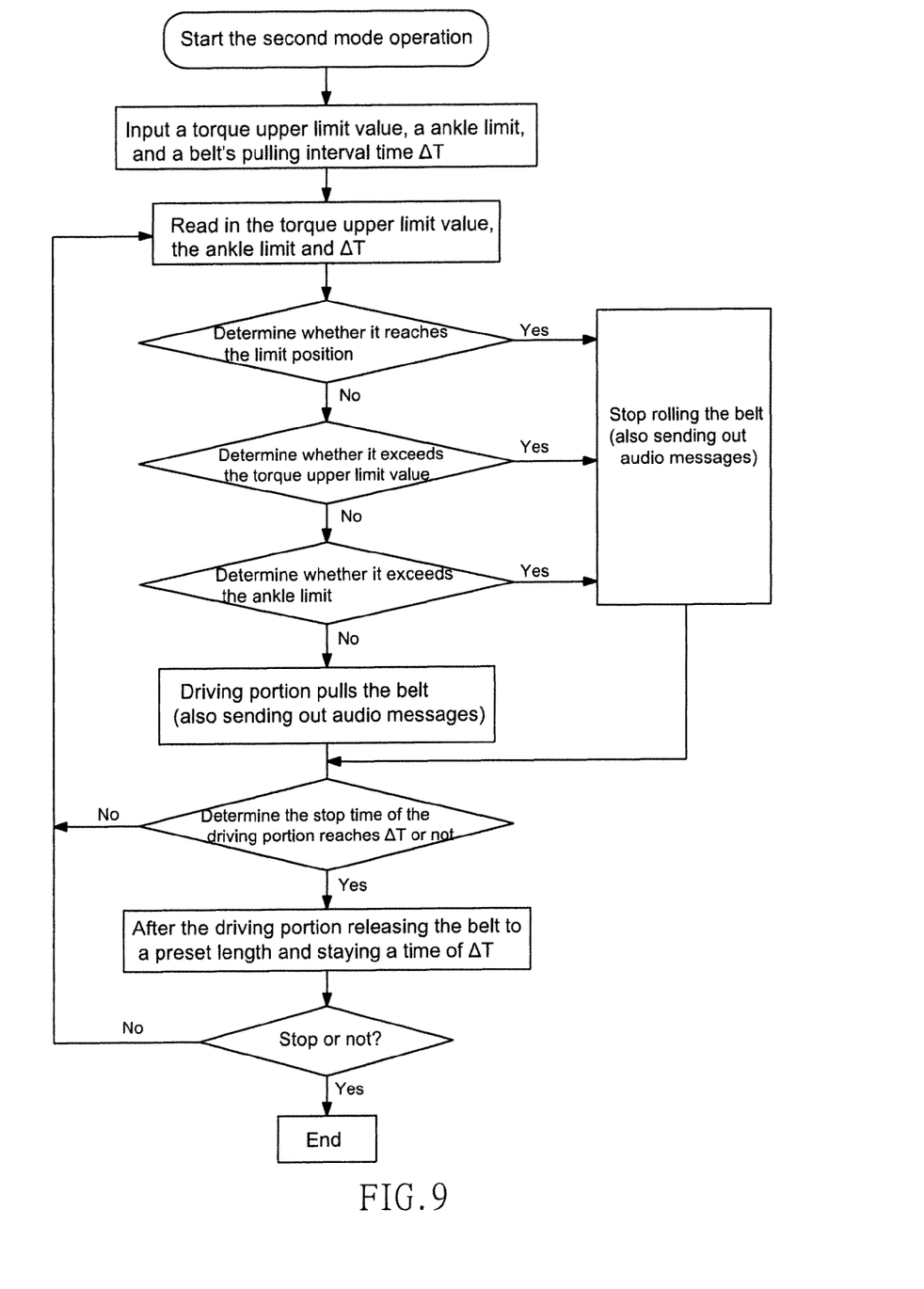
FIG. 9 shows a flowchart of the second operation of this invention.
Figure 10B:
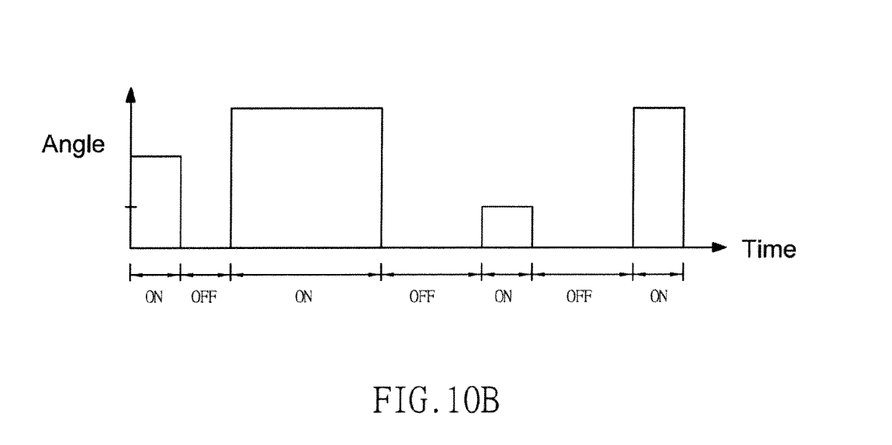
FIG. 10B shows the relationship between the rotation angle and time in the second operation mode.

[b] Variation operation mode (or called the second operation mode). As illustrated in FIGS. 9 and 10B, the user can input another torque upper limit value, another ankle limit via, and a belt's (which is the second end portion 42) pulling interval time ΔT via the input portion 433. After which, the driving portion 435 is turned on. Then, the foot will be pulled by different desired angles/times (ON) and be released with different resting times (OFF). In this mode, the pulling angle, time, and different pulling interval time ΔT can be set by the user. Such variation of pulling actions can increase the variety of intrinsic toe exercise.

The advantages and functions of this invention can be summarized as follows.

[1] It can achieve an active rehabilitation exercise. Because this invention has a driving portion, the foot of the user can be pulled by this invention. It saves a lot of physical strength. In addition, the torque upper limit value and the ankle limit can be set up for preventing injuring the user's foot and ankle as well as for effectuating the plantar fasciitis rehabilitation. During the exercise, the user's hand does not need to contact with the foot. It is quite easy.

[2] The belt's pulling interval time can be adjusted. The pulling time (ON) and non-pulling time (OFF) can be set depending on the user's input. Once it pulls longer, the rotation angle becomes larger. Therefore, not only the torque upper limit value and the ankle limit can be set, but also the pulling interval time can be set. Hence, under such circumstances, different pulling degree, lasting time, and rest time can be adjustable. So, the variety of the rehabilitation process is raised.

[3] It has a safety switch to ensure its product safety. In case the user's leg has a spasm or becomes quite uncomfortable, the user can turn on the safety switch to stop all exercise. Thus, it is very safe.

[4] It is convenient that the user can use a wireless device to operate this system. By utilizing the wireless device, the user can operate this system without using fingers to touch the controller. It is convenient.

[5] The user can be informed about current condition via an audio device. Because of the audio device, it is possible to let the user know the current condition without watching the display.

While we have shown and described the embodiment in accordance with the present invention, it should be clear to those skilled in the art that further embodiments may be made without departing from the scope of the present invention.

What is claimed is:

1. A plantar fasciitis rehabilitation controlling device comprising:
a securing portion for securing a user's shank; said securing portion having a pivoting part;
a rotatable portion for securing a user's foot; said rotatable portion having a pair of pivoting receivers;
a torque pivoting portion connected with said securing portion and said rotatable portion so as to create a torque causing said rotatable portion moving back;

a pulling portion having a first end portion and a second end, said first end portion being pivoted on said securing portion, said second end portion connecting with said rotatable portion; and a controller being disposed between said first end portion and said second end portion so as to pull said rotatable portion to rotate between a first angle and a second angle so that it can reduce possibility of plantar fasciitis occurrence or reduce symptoms of plantar fasciitis;

wherein said torque pivoting portion includes:
- a shaft being disposed in said pivoting part and said pivoting receivers, said shaft being pivoted with said securing portion and said rotatable portion;
- a torque element fitting on said shaft, said torque element being a torque spring for generating a force to pull said rotatable portion back, said torque element at least including a touching end; and
- a limit controller including one limit switch responding to said first angle and another limit switch responding to said second angle.

2. The plantar fasciitis rehabilitation controlling device as claimed in claim 1, further comprising:
- a locking portion having a male locker and a female locker, said locking portion being disposed on said second end;
- an audio device for generating voice messages about current condition; and
- a wireless device including a wireless transmitter and a wireless receiver which is electrically connected to said controller; and
- a safety switch for deactivating said pulling portion.

3. The plantar fasciitis rehabilitation controlling device as claimed in claim 1, wherein
said second end portion is a resilient belt; and
said controller including:
- a power source which is a battery for providing power to said controller;
- a controlling circuit module having a central processing unit, a random access memory, and a read only memory; said controlling circuit module being provided for pulling/releasing said rotatable portion;
- an input portion for inputting at least one controlling information to said controlling circuit module;
- a display for showing said controlling information of said input portion;
- a driving portion which is an electric motor controlled by said controlling circuit module according to said controlling information;
- a reduction device to reduce an output of said driving portion into another slower output; and
- a rolling portion which is a pulley, said second end portion of said rolling portion being pulled/released by said reduction device so as to rotate said rotatable portion.

4. The plantar fasciitis rehabilitation controlling device as claimed in claim 3, wherein said pulling portion includes:
- a torque sensor connecting with said rolling portion for detecting torque and sending out a signal to said controller via an analog/digital converter; and
- an angle detector disposed on said pivoting portion for detecting rotation angle of said rotatable portion and sending out another signal to said controller via another analog/digital converter.

5. A plantar fasciitis rehabilitation controlling device comprising:
- a securing portion for securing a user's shank;
- a rotatable portion for securing a user's foot;
- a torque pivoting portion connected with said securing portion and said rotatable portion so as to create a torque causing said rotatable portion moving back;
- a pulling portion having a first end portion and a second end, said first end portion being pivoted on said securing portion, said second end portion connecting with said rotatable portion; and
- a controller being disposed between said first end portion and said second end portion so as to pull said rotatable portion to rotate between a first angle and a second angle so that it can reduce possibility of plantar fasciitis occurrence or reduce symptoms of plantar fasciitis;

wherein said pulling portion includes:
- a torque sensor connecting with a rolling portion defining a pulley for detecting torque and sending out a signal to said controller via an analog/digital converter; and
- an angle detector disposed on said pivoting portion for detecting rotation angle of said rotatable portion and sending out another signal to said controller via another analog/digital converter.

6. The plantar fasciitis rehabilitation controlling device as claimed in claim 5, further comprising:
- a locking portion having a male locker and a female locker, said locking portion being disposed on said second end;
- an audio device for generating voice messages about current condition;
- a wireless device including a wireless transmitter and a wireless receiver which is electrically connected to said controller; and
- a safety switch for deactivating said pulling portion.

7. The plantar fasciitis rehabilitation controlling device as claimed in claim 5, wherein said securing portion having a pivoting part;
said rotatable portion having a pair of pivoting receivers; and
said torque pivoting portion including:
- a shaft being disposed in said pivoting part and said pivoting receivers, said shaft being pivoted with said securing portion and said rotatable portion;
- a torque element fitting on said shaft, said torque element being a torque spring for generating a force to pull said rotatable portion back, said torque element at least including a touching end; and
- a limit controller including one limit switch responding to said first angle and another limit switch responding to said second angle.

8. The plantar fasciitis rehabilitation controlling device as claimed in claim 5, wherein
said second end portion is a resilient belt; and
said controller including:
- a power source which is a battery for providing power to said controller;
- a controlling circuit module having a central processing unit, a random access memory, and a read only memory; said controlling circuit module being provided for pulling/releasing said rotatable portion;
- an input portion for inputting at least one controlling information to said controlling circuit module;
- a display for showing said controlling information of said input portion;
- a driving portion which is an electric motor controlled by said controlling circuit module according to said controlling information;
- a reduction device to reduce an output of said driving portion into another slower output; and a rolling portion which is a pulley, said second end portion of said rolling portion being pulled/released by said reduction device so as to rotate said rotatable portion.

9. A plantar fasciitis rehabilitation controlling device comprising:

a securing portion for securing a user's shank;

a rotatable portion for securing a user's foot;

a torque pivoting portion connected with said securing portion and said rotatable portion so as to create a torque causing said rotatable portion moving back;

a pulling portion having a first end portion and a second end, said first end portion being pivoted on said securing portion, said second end portion connecting with said rotatable portion;

a controller being disposed between said first end portion and said second end portion so as to pull said rotatable portion to rotate between a first angle and a second angle so that it can reduce possibility of plantar fasciitis occurrence or reduce symptoms of plantar fasciitis;

a locking portion having a male locker and a female locker, said locking portion being disposed on said second end;

an audio device for generating voice messages about current condition;

a wireless device including a wireless transmitter and a wireless receiver which is electrically connected to said controller; and a safety switch for deactivating said pulling portion.

10. The plantar fasciitis rehabilitation controlling device as claimed in claim 9, wherein said pulling portion includes:

a torque sensor connecting with said rolling portion for detecting torque and sending out a signal to said controller via an analog/digital converter; and an angle detector disposed on said pivoting portion for detecting rotation angle of said rotatable portion and sending out another signal to said controller via another analog/digital converter.

11. The plantar fasciitis rehabilitation controlling device as claimed in claim 9, wherein said securing portion having a pivoting part;

said rotatable portion having a pair of pivoting receivers; and said torque pivoting portion including:

a shaft being disposed in said pivoting part and said pivoting receivers, said shaft being pivoted with said securing portion and said rotatable portion;

a torque element fitting on said shaft, said torque element being a torque spring for generating a force to pull said rotatable portion back, said torque element at least including a touching end; and a limit controller including one limit switch responding to said first angle and another limit switch responding to said second angle.

12. The plantar fasciitis rehabilitation controlling device as claimed in claim 9, wherein said second end portion is a resilient belt; and said controller including:

a power source which is a battery for providing power to said controller;

a controlling circuit module having a central processing unit, a random access memory, and a read only memory; said controlling circuit module being provided for pulling/releasing said rotatable portion;

an input portion for inputting at least one controlling information to said controlling circuit module;

a display for showing said controlling information of said input portion;

a driving portion which is an electric motor controlled by said controlling circuit module according to said controlling information;

a reduction device to reduce an output of said driving portion into another slower output; and a rolling portion which is a pulley, said second end portion of said rolling portion being pulled/released by said reduction device so as to rotate said rotatable portion.

* * * * *